(12) United States Patent
Lee et al.

(10) Patent No.: US 10,837,043 B2
(45) Date of Patent: Nov. 17, 2020

(54) METHOD FOR PRODUCING COENZYME Q10

(71) Applicant: KANEKA CORPORATION, Osaka-shi (JP)

(72) Inventors: Wan Ying Lee, Takasago (JP); Yasuyuki Suzuki, Takasago (JP); Akihisa Kanda, Takasago (JP)

(73) Assignee: KANEKA CORPORATION, Osaka (JP)

(*) Notice: Subject to any disclaimer, the term of this patent is extended or adjusted under 35 U.S.C. 154(b) by 28 days.

(21) Appl. No.: 16/233,392

(22) Filed: Dec. 27, 2018

(65) Prior Publication Data

US 2019/0127773 A1 May 2, 2019
US 2020/0208189 A9 Jul. 2, 2020

Related U.S. Application Data

(63) Continuation of application No. PCT/JP2017/024154, filed on Jun. 30, 2017.

(30) Foreign Application Priority Data

Jul. 1, 2016 (JP) .................................. 2016-131817

(51) Int. Cl.
*B01D 15/00* (2006.01)
*B01J 20/16* (2006.01)
*B01J 20/18* (2006.01)
*B01J 20/20* (2006.01)
*B01J 20/22* (2006.01)
*B01J 20/26* (2006.01)
*C12P 23/00* (2006.01)
*C12P 7/66* (2006.01)

(52) U.S. Cl.
CPC .............. *C12P 23/00* (2013.01); *B01D 15/00* (2013.01); *B01J 20/16* (2013.01); *B01J 20/18* (2013.01); *B01J 20/20* (2013.01); *B01J 20/22* (2013.01); *B01J 20/26* (2013.01); *C12P 7/66* (2013.01)

(58) Field of Classification Search
CPC .... C12P 23/00; C12P 7/66; B01J 20/26; B01J 20/16; B01J 20/20; B01J 20/22; B01J 20/18; B01D 15/00; B01D 9/00; B01D 9/0059; B01D 2009/0086; B01D 2009/009; B01D 11/02; B01D 11/028; B01D 11/0288; B01D 15/08; B01D 15/10; B01D 15/12; B01D 15/265; B01D 17/0202; B01D 36/02; B01D 37/00; A61K 8/66; A61K 38/43; A61K 38/53; C11B 3/001; C11B 3/006; C11B 3/008; C11B 3/10; C11B 7/00; C11B 7/0008; C11B 9/02; C11B 9/025
USPC ....... 210/634, 639, 656, 660, 663, 690, 691, 210/694, 702, 757, 758, 774, 806; 554/175, 176, 191, 194, 196, 198; 426/417, 478, 479, 481; 424/94.1, 94.2, 424/195.15, 780; 23/295, 295 R, 296, 23/297
See application file for complete search history.

(56) References Cited

U.S. PATENT DOCUMENTS

| | | | | |
|---|---|---|---|---|
| 2,348,037 A * | 5/1944 | Thayer | ..................... | C07C 46/04 552/299 |
| 2,882,244 A * | 4/1959 | Milton | ..................... | B01J 20/18 423/718 |
| 3,658,648 A * | 4/1972 | Nakao | ..................... | C12P 7/66 435/133 |
| 3,769,170 A * | 10/1973 | Kondo | ..................... | C12P 7/66 435/133 |
| 4,073,883 A * | 2/1978 | Yasuda | .................. | A61K 31/12 424/94.1 |
| 4,205,125 A * | 5/1980 | Aida | ..................... | C12P 7/66 435/133 |
| 6,464,770 B1 * | 10/2002 | Palm | ..................... | B01D 39/06 106/409 |
| 7,910,340 B2 * | 3/2011 | Yajima | ..................... | C12P 7/66 435/133 |
| 9,039,898 B2 * | 5/2015 | Song | ..................... | A23D 9/02 210/634 |
| 9,315,839 B2 * | 4/2016 | Yajima | ..................... | C12P 7/66 |
| 9,926,580 B2 * | 3/2018 | Yajima | ..................... | C12P 7/66 |
| 2007/0025976 A1 | 2/2007 | Kluetz et al. | | |
| 2013/0225868 A1 * | 8/2013 | Kanaya | ..................... | C12P 7/66 568/377 |
| 2015/0284311 A1 | 10/2015 | Kawachi et al. | | |

FOREIGN PATENT DOCUMENTS

| | | |
|---|---|---|
| EP | 2 597 156 A1 | 5/2013 |
| GB | 930752 A | 7/1963 |
| JP | 48-21519 | 6/1973 |
| JP | 51-32788 | 3/1976 |

(Continued)

OTHER PUBLICATIONS

Eguchi et al, Translated Abstract of Publication JP 55-27114, Feb. 1980 (Year: 1980).*

(Continued)

*Primary Examiner* — Joseph W Drodge
(74) *Attorney, Agent, or Firm* — Oblon, McClelland, Maier & Neustadt, L.L.P.

(57) ABSTRACT

A method of producing coenzyme Q10 includes contacting an extract from a coenzyme Q10-producing microorganism with an adsorbent (A) such that the adsorbent (A) adsorbs a component of the extract other than coenzyme Q10, and that coenzyme Q10 is obtained. The adsorbent (A) includes aluminum silicate at a content of 50% or more.

20 Claims, No Drawings

(56) References Cited

FOREIGN PATENT DOCUMENTS

| JP | 54-46889 | | 4/1979 | | |
|----|----------|---|--------|---|---|
| JP | 55-27114 | * | 2/1980 | ............. | C07C 50/28 |
| JP | 55-39701 | | 3/1980 | | |
| JP | 59-173088 | | 9/1984 | | |
| JP | 2015-131766 | | 7/2015 | | |

OTHER PUBLICATIONS

Extended European Search Report dated Jan. 7, 2020 in European Patent Application No. 17820328.7, citing documents AA, AO, AP and AX therein, 9 pages.

Cao, X.-L., et al., "Purification of Coenzyme $Q_{10}$ from Fermentation Extract: High-speed counter-current chromatography versus silica gel column chromatography", Science Direct, Journal of Chromatography A, vol. 1127 No. 1-2, Sep. 15, 2006, XP024967634, pp. 92-96.

A translation of the Japanese term "" on an online dictionary, Eijiro on the Web, available at https://eow.alc.co.jp/ (as of Jun. 2, 2020)—4 pages.

\* cited by examiner

METHOD FOR PRODUCING COENZYME Q10

CROSS-REFERENCE TO RELATED APPLICATIONS

The present application is a continuation of International Application No. PCT/JP2017/024154, filed Jun. 30, 2017, which is based upon and claims the benefits of priority to Japanese Application No. 2016-131817, filed Jul. 1, 2016. The entire contents of these applications are incorporated herein by reference.

BACKGROUND OF THE INVENTION

Field of the Invention

The present invention relates to a method for producing coenzyme Q10. More specifically, the present invention relates to a method for producing coenzyme Q10 by using an adsorbent to remove impurity from an extract of a coenzyme Q10-producing microorganism.

Discussion of the Background

Coenzyme Q is an essential component which is widely distributed in a living body of from a bacterium to a mammal and is known as a constituent of an electron transport system of mitochondria in living body cells. Coenzyme Q repeats an oxidation and reduction to play a role as a messenger component in an electron transport system in a mitochondria. In addition, it is known that reduced coenzyme Q has an antioxidant property. Human coenzyme Q contains coenzyme Q10 having 10 repetitive structures in the side chain as a main component, and generally about 40 to 90% of human coenzyme Q exists as a reduced type in a living body. A physiological function of coenzyme Q is exemplified by an activation of an energy production by activating a mitochondria, an activation of cardiac function, a stabilization of a cell membrane, and a protection of cells by antioxidant action.

Many of the coenzyme Q10 which is currently manufactured and marketed are oxidized type, but recently reduced coenzyme Q10 having higher oral absorbability than oxidized coenzyme Q10 appears on the market and has been widely used.

Some of methods for producing coenzyme Q10 have been known. For example, Patent document 1 discloses a method for producing reduced coenzyme Q10 by crystalizing reduced coenzyme Q10 from a solution containing reduced coenzyme Q10 with cooling crystallization, poor solvent crystallization, or a combination of cooling crystallization and other crystallization method.

In addition, Patent document 2 discloses a method for producing coenzyme Q10 by repeating an extraction treatment in which coenzyme Q10-containing substance is contacted with a hydrophilic solvent in the presence of water and an adsorption treatment to adsorb coenzyme Q10 in the coenzyme Q10 extract obtained by the extraction treatment on a hydrophobic adsorbent.

Patent document 1: JP 2015-131766 A
Patent document 2: JP S59-173088 A

SUMMARY OF THE INVENTION

According to an aspect of the present invention, a method of producing coenzyme Q10 includes contacting an extract from a coenzyme Q10-producing microorganism with an adsorbent (A) such that the adsorbent (A) adsorbs a component of the extract other than coenzyme Q10, and that coenzyme Q10 is obtained. The adsorbent (A) includes aluminum silicate at a content of 50% or more.

DESCRIPTION OF THE EMBODIMENTS

The embodiments will now be described with reference to the accompanying drawings, wherein like reference numerals designate corresponding or identical elements throughout the various drawings.

Hereinafter, one embodiment of the method for producing coenzyme Q10 according to the present invention is described, but the present invention is not restricted thereto.

The production method according to one embodiment of the present invention is characterized in contacting an extract of a coenzyme Q10-producing microorganism with an adsorbent (A), wherein a main component of the adsorbent (A) is aluminum silicate.

Coenzyme Q10 has an oxidized form and a reduced form. The target is both of oxidized coenzyme Q10 and reduced coenzyme Q10 as coenzyme Q10, and coenzyme Q10 containing both of oxidized coenzyme Q10 and reduced coenzyme Q10 is also the target. When coenzyme Q10 is a mixture of oxidized coenzyme Q10 and reduced coenzyme Q10, a content ratio of reduced coenzyme Q10 is not particularly restricted.

The description of mere "coenzyme Q10" in this disclosure is not restricted to either of oxidized coenzyme Q10 or reduced coenzyme Q10, and when oxidized coenzyme Q10 and reduced coenzyme Q10 are mixed, the coenzyme Q10 means any mixture.

As the coenzyme Q10-producing microorganism usable in the present invention, any one of bacteria, yeast and fungus may be used without limitation as long as the microorganism can produce coenzyme Q10 in the cells. Such a microorganism is specifically exemplified by a microorganism belonging to genera of *Acetobacter, Aminobacter, Agromonas, Acidiphilium, Bulleromyces, Bullera, Brevundimonas, Cryptococcus, Chionosphaera, Candida, Cerinosterus, Exisophiala, Exobasidium, Fellomyces, Filobasidiella, Filobasidium, Geotrichum, Graphiola, Gluconobacter, Kockovaella, Kurtzmanomyces, Lalaria, Leucosporidium, Legionella, Methylobacterium, Mycoplana, Oosporidium, Pseudomonas, Psedozyma, Paracoccus, Petromyc, Rhodotorula, Rhodosporidium, Rhizomonas, Rhodobium, Rhodoplanes, Rhodopseudomonas, Rhodobacter, Sporobolomyces, Sporidiobolus, Saitoella, Schizosaccharomyces, Sphingomonas, Sporotrichum, Sympodiomycopsis, Sterigmatosporidium, Tapharina, Tremella, Trichosporon, Tilletiaria, Tilletia, Tolyposporium, Tilletiopsis, Ustilago, Udeniomyce, Xanthophllomyces, Xanthobacter, Paecilomyces, Acremonium, Hyhomonus, Rhizobium, Phaffia* and *Haematococcus*. From the aspect of easy cultivation and productivity, bacteria and yeast are preferred. As bacteria, non-photosynthetic bacteria is preferred, and bacteria belonging to genera of *Agrobacterium* and *Gluconobacter* are preferred. As yeast, a yeast belonging to genera of *Schizosaccharomyces, Saitoella* and *Phaffia* are particularly preferred. When reduced coenzyme Q10 is purposely produced as coenzyme Q10, it is preferred to use a microorganism by which produced coenzyme Q has high content ratio of reduced coenzyme Q. For example, it is more preferred to use a microorganism of which content ratio by weight of reduced coenzyme Q after cultivation is preferably 70% or more and more preferably 80% or more.

As the coenzyme Q10-producing microorganism, not only a wild strain of the above-described microorganism but also a variant and a recombinant of the above-described microorganism of which transcription activity and translation activity of a gene involved in a biosynthesis of the target coenzyme Q10 and an enzyme activity of an expressed protein is altered or improved can be used.

By cultivating the above-described microorganism, microorganism cells containing coenzyme Q10 can be obtained. A cultivating method is not particularly restricted, and a cultivating method suitable for the target microorganism or the production of the target coenzyme Q10 can be appropriately selected. A cultivation time is also particularly not restricted, and may be adjusted to the range that a desired amount of the target coenzyme Q10 is accumulated in microorganism cells.

As the method for extracting coenzyme Q10 from the above-described microorganism cells, coenzyme Q10 can be directly extracted from the microorganism cells, or the microorganism cells are homogenized to obtain a microorganism cell homogenate or an aqueous dispersion of a microorganism cell homogenate and coenzyme Q10 can be extracted from the homogenate or the microorganism cell homogenate aqueous dispersion. Alternatively, the microorganism cells are dried and coenzyme Q10 can be extracted from the dried microorganism cell. In the "homogenization" according to embodiments of the present invention, the surface structure of a cell wall or the like is damaged so that it becomes possible to extract the target coenzyme Q10.

The homogenization method is exemplified by physical treatment and chemical treatment.

The above-described physical treatment is exemplified by a treatment using high pressure homogenizer, rotary blade homogenizer, ultrasonic homogenizer, French press, ball mill or the like, and a combination thereof.

The above-described chemical treatment is exemplified by a treatment using an acid such as hydrochloric acid and sulfuric acid, preferably a strong acid, a base such as sodium hydroxide and potassium hydroxide, preferably a strong base, and a combination thereof.

As a method for homogenizing cells as a pretreatment for the extraction and recovery of coenzyme Q10, a physical treatment is more preferred among the above-described homogenization methods in terms of a homogenization efficiency.

A form of the microorganism cells used for the above-described cell homogenization may be a culture medium, a concentrated culture medium, wet cells, washed wet cells, or a wet cell dispersion, preferably an aqueous dispersion of the microorganism cells, and more preferably a culture medium, a concentrated culture medium, a washed culture medium, and a washed concentrated culture medium in terms of handling property. The wet cells are the microorganism cells collected from a culture medium. A solvent of the microorganism cell aqueous dispersion is exemplified by water, a saline solution and a buffer solution.

A cell concentration in the aqueous dispersion of the microorganism cell homogenate is not particularly restricted, and the concentration in terms of the weight of the dried cells is generally in a range of 1 to 25 wt %, and preferably in a range of 10 to 20 wt % from a viewpoint of economy.

When the microorganism cells are dried and coenzyme Q10 is extracted from the dried microorganism cells, a dryer for drying the microorganism cells is exemplified by fluidized dryer, spray dryer, box dryer, cone dryer, cylindrical vibration dryer, cylindrical agitating dryer, inverse cone dryer, filter dryer, freeze dryer, and a combination thereof.

It is preferred that a water concentration in the dried microorganism cells is included in a range of 0 to 50 wt %. In addition, a dried microorganism homogenate prepared by homogenizing the dried microorganism cells with the above-described homogenization method or drying the above-described microorganism cell homogenate can be also used.

An organic solvent usable for the extraction is not particularly restricted and exemplified by a hydrocarbon solvent, a fatty acid ester solvent, an ether solvent, an alcohol solvent, a fatty acid solvent, a ketone solvent, a nitrogen compound solvent such as a nitrile solvent and an amide solvent, and a sulfur compound solvent.

A hydrocarbon solvent is not particularly restricted and is exemplified by an aliphatic hydrocarbon solvent, an aromatic hydrocarbon solvent and a halogenated hydrocarbon solvent. Among the examples, an aliphatic hydrocarbon solvent and an aromatic hydrocarbon solvent are preferred, and an aliphatic hydrocarbon solvent is more preferred.

An aliphatic hydrocarbon solvent may be cyclic or noncyclic and saturated or unsaturated, is not particularly restricted, and a saturated aliphatic hydrocarbon solvent is generally used. In general, a $C_{3-20}$ aliphatic hydrocarbon solvent is used, a $C_{5-12}$ aliphatic hydrocarbon solvent is preferably used, and a $C_{5-8}$ aliphatic hydrocarbon solvent is more preferably used. Specifically, propane, butane, isobutane, pentane, 2-methylbutane, hexane, 2-methylpentane, 2,2-dimethylbutane, 2,3-dimethylbutane, heptane, a heptane isomer such as 2-methylhexane, 3-methylhexane, 2,3-dimethylpentane and 2,4-dimethylpentane, octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane and cyclohexene are exemplified. Preferably, pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane and p-menthane are exemplified. More preferably, pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane and ethylcyclohexane are exemplified. More preferably, pentane, hexane, cyclohexane and methylcyclohexane are exemplified. Particularly preferably, heptane and methylcyclohexane are exemplified, since a protection effect from oxidation is very high. Most preferably, heptane is exemplified.

An aromatic hydrocarbon solvent is not particularly restricted, and a $C_{6-20}$ aromatic hydrocarbon solvent is generally used, a $C_{6-12}$ aromatic hydrocarbon solvent is preferably used, and a $C_{7-10}$ aromatic hydrocarbon solvent is more preferably used. Specifically, an aromatic hydrocarbon solvent is exemplified by benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene and styrene, preferably toluene, xylene, o-xylene, m-xylene, p-xylene, ethylbenzene, cumene, mesitylene, tetralin, butylbenzene, p-cymene, cyclohexylbenzene, diethylbenzene and pentylbenzene, more preferably toluene, xylene, o-xylene, m-xylene, p-xylene, cumene and tetralin, and most preferably cumene.

A halogenated hydrocarbon solvent may be cyclic or non-cyclic and saturated or unsaturated, is not particularly restricted, and a non-cyclic halogenated hydrocarbon solvent is preferably used. A halogenated hydrocarbon solvent is more preferably a chlorinated hydrocarbon and a fluorinated hydrocarbon, and even more preferably a chlorinated hydrocarbon. In addition, a $C_{1-6}$ halogenated hydrocarbon solvent may be used, a $C_{1-4}$ halogenated hydrocarbon solvent is preferably used, and a $C_{1-2}$ halogenated hydrocarbon solvent is more preferably used. Specifically, a halogenated hydrocarbon solvent is exemplified by dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene and 1,1,1,2-tetrafluoroethane, preferably dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane, more preferably dichloromethane, chloroform, 1,2-dichloroethylene, trichloroethylene, chlorobenzene and 1,1,1,2-tetrafluoroethane.

A fatty acid ester solvent is not particularly restricted, and is exemplified by a propionate ester, an acetate ester and a formate ester, preferably an acetate ester and a formate ester, and more preferably an acetate ester. An ester group is not particularly restricted, and a $C_{1-8}$ alkyl ester and a $C_{7-12}$ aralkyl ester are generally used, a $C_{1-6}$ alkyl ester is preferably used, and a $C_{1-4}$ alkyl ester is more preferably used.

A propionate ester is specifically exemplified by methyl propionate, ethyl propionate, butyl propionate and isopentyl propionate, and preferably ethyl propionate.

An acetate ester is specifically exemplified by methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate and benzyl acetate, preferably methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate, more preferably methyl acetate, ethyl acetate, propyl acetate, isopropyl acetate, butyl acetate and isobutyl acetate, and most preferably ethyl acetate.

A formate ester is specifically exemplified by methyl formate, ethyl formate, propyl formate, isopropyl formate, butyl formate, isobutyl formate, sec-butyl formate and pentyl formate, preferably methyl formate, ethyl formate, propyl formate, butyl formate, isobutyl formate and pentyl formate, and most preferably ethyl formate.

An ether solvent may be cyclic or non-cyclic and saturated or unsaturated, is not particularly restricted, and a saturated ether solvent is preferably used. In general, a $C_{3-20}$ ether solvent is used, a $C_{4-12}$ ether solvent is preferably used, and a $C_{4-8}$ ether solvent is more preferably used. An ether solvent is specifically exemplified by diethyl ether, methyl tert-butyl ether, dipropyl ether, diisopropyl ether, dibutyl ether, dihexyl ether, ethyl vinyl ether, butyl vinyl ether, anisole, phenetol, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether and ethylene glycol monobutyl ether, preferably diethyl ether, methyl tert-butyl ether, dipropyl ether, diisopropyl ether, dibutyl ether, dihexyl ether, anisole, phenetol, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether, more preferably diethyl ether, methyl tert-butyl ether, anisole, dioxane, tetrahydrofuran, ethylene glycol monomethyl ether and ethylene glycol monoethyl ether, more preferably diethyl ether, methyl tert-butyl ether and anisole, and most preferably methyl tert-butyl ether.

An alcohol solvent may be cyclic or non-cyclic and saturated or unsaturated, is not particularly restricted, and a saturated alcohol solvent is generally used. In general, a $C_{1-20}$ alcohol solvent is used, a $C_{1-12}$ alcohol solvent is preferably used, and a $C_{1-6}$ alcohol solvent is more preferably used. In particular, a $C_{1-5}$ monovalent alcohol solvent, a $C_{2-5}$ divalent alcohol solvent and a $C_3$ trivalent alcohol solvent are preferred.

An alcohol solvent is specifically exemplified by a monovalent alcohol such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol and 4-methylcyclohexanol; a divalent alcohol solvent such as 1,2-ethanediol, 1,2-propanediol, 1,3-propanediol, 1,2-butanediol, 1,3-butanediol, 1,4-butanediol, 2,3-butanediol and 1,5-pentanediol; and a trivalent alcohol such as glycerin.

A monovalent alcohol is preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol or 4-methylcyclohexanol, more preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol or cyclohexanol, more preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol or neopentyl alcohol, particularly preferably methanol, ethanol, 1-propanol, 2-propanol, 1-butanol, 2-butanol, isobutyl alcohol, 2-methyl-1-butanol or isopentyl alcohol, and most preferably 2-propanol.

A divalent alcohol is preferably 1,2-ethanediol, 1,2-propanediol or 1,3-propanediol, and most preferably 1,2-ethanediol. A trivalent alcohol is preferably glycerin.

A fatty acid solvent is exemplified by formic acid, acetic acid and propionic acid, preferably formic acid and acetic acid, and most preferably acetic acid.

A ketone solvent is not particularly restricted, and a $C_{3-6}$ ketone solvent is preferably used. A ketone solvent is specifically exemplified by acetone, methyl ethyl ketone, methyl butyl ketone and methyl isobutyl ketone, preferably acetone and methyl ethyl ketone, and most preferably acetone.

A nitrile solvent may be cyclic or non-cyclic and saturated or unsaturated, is not particularly restricted, and a saturated nitrile solvent is generally used. In general, a $C_{2-20}$ nitrile solvent is used, a $C_{2-12}$ nitrile solvent is preferably used, and a $C_{2-8}$ nitrile solvent is more preferably used.

A nitrile solvent is specifically exemplified by acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenyl cyclohexanecarbonitrile and tolylcyclohexanecarbonitrile.

A nitrile solvent is preferably acetonitrile, propionitrile, succinonitrile, butyronitrile, isobutyronitrile, valeronitrile, methyl cyanoacetate, ethyl cyanoacetate, benzonitrile, tolunitrile or chloropropionitrile, more preferably acetonitrile, propionitrile, butyronitrile or isobutyronitrile, and most preferably acetonitrile.

A nitrogen compound solvent except for a nitrile solvent is exemplified by an amide solvent such as formamide, N-methylformamide, N,N-dimethylformamide, N,N-dimethylacetamide and N-methylpyrrolidone; nitromethane; triethylamine; and pyridine.

A sulfur compound solvent is exemplified by dimethyl sulfoxide and sulfolane.

It is preferred to select an organic solvent in consideration of the boiling point, melting point, viscosity or the like. For example, it is preferred that the boiling point is included in the range of about 30 to 150° C. at 1 atmospheres, since a solvent having such a boiling point can be moderately heated for increasing a solubility and the solvent can be easily removed for drying wet cells and recovered from a filtrate after crystallization. The melting point may be about 0° C. or higher, preferably about 10° C. or higher, and more preferably about 20° C. or higher, since a solvent is hardly solidified in the case of using the solvent at room temperature and cooling the solvent to room temperature or lower. The viscosity is preferably low as about 10 cp or lower at 20° C.

When coenzyme Q10 is extracted from the microorganism cells or an aqueous dispersion of the microorganism cell homogenate, it is preferred to use a hydrophobic organic solvent or a solvent containing a hydrophobic organic solvent as an extraction solvent. When a small amount of a hydrophilic organic solvent or a surfactant is added to a hydrophobic organic solvent to be used, an extraction efficiency may be further increased. Such a hydrophilic organic solvent is exemplified by an alcohol solvent such as isopropanol.

The hydrophobic organic solvent used in the above-described case is not particularly restricted, and a hydrophobic solvent among the above-described organic solvent may be used. The hydrophobic organic solvent is preferably exemplified by a hydrocarbon solvent, an aliphatic acid ester solvent and an ether solvent, more preferably an aliphatic acid ester solvent and a hydrocarbon solvent, and even more preferably an aliphatic hydrocarbon solvent. Among the aliphatic hydrocarbon solvent, a $C_{5-8}$ aliphatic hydrocarbon solvent is preferably used. The $C_{5-8}$ aliphatic hydrocarbon solvent is specifically exemplified by pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane and ethylcyclohexane, particularly preferably hexane, heptane and methylcyclohexane, and most preferably hexane. As the aliphatic acid ester solvent, ethyl acetate is preferably used.

When coenzyme Q10 is extracted from the dried microorganism cells, the above-described hydrophobic organic solvent or a solvent containing the hydrophobic organic solvent is also preferably used as an extraction solvent but a hydrophilic organic solvent can be also used. Such a hydrophilic organic solvent is not particularly restricted and is more preferably the above-described alcohol solvent and ketone solvent. The alcohol solvent is not particularly restricted, and methanol, ethanol, propanol, butanol and glycerin are preferred. As the ketone solvent, acetone is preferred. Among the examples, ethanol is the most preferred.

An amount of the extraction solvent is not particularly restricted, and the concentration to the entire solution volume at the time of the extraction is preferably in the range of 25 to 80 vol %, and more preferably in the range of 50 to 75 vol %. A temperature at the time of the extraction is not particularly restricted and may be generally in the range of 0 to 60° C. and preferably in the range of 20 to 50° C.

An extraction method may be any one of batch extraction and continuous extraction, and continuous extraction is industrially preferred in terms of a productivity. Among continuous extraction, countercurrent multistep extraction is particularly preferred. A stirring time in the case of batch extraction is not particularly restricted and may be generally 5 minutes or longer. An average residence time in the case of continuous extraction is not particularly restricted and may be generally 10 minutes or longer.

The thus obtained extract itself from the coenzyme Q10-producing microorganism may be directly used as a coenzyme Q10 solution. The extract may be appropriately concentrated, diluted, or the solvent in the extract may be replaced by other solvent to obtain a coenzyme Q10 solution. The coenzyme Q10 solution is contacted with an adsorbent (A) in order to selectively adsorb impurity to be removed. The adsorbent (A) hardly adsorbs coenzyme Q10 but can adsorb impurity, and a main component of the adsorbent (A) is aluminum silicate.

The adsorbent (A) is not particularly restricted as long as a main component of the adsorbent is aluminum silicate. The aluminum silicate may be any one of natural aluminum silicate and synthetic aluminum silicate. The adsorbent (A) may be composed of aluminum silicate only or contain aluminum silicate as a main component and other component. The adsorbent (A) contains aluminum silicate preferably in 50% by weight or more, more preferably 60% by weight or more, and even more preferably 65% by weight or more. In addition, a plurality of the above-described aluminum silicate may be mixed to be used. With respect to the adsorbent (A) used in the present invention production method, among the above-described aluminum silicate, amorphous synthetic aluminum silicate is preferred, and aluminum silicate having a chemical composition in which a ratio of silicon dioxide is 50 to 70% and further 55 to 65% is preferred. In addition, it is preferred that there is a little crystal water in aluminum silicate. For example, a drying loss of aluminum silicate is preferably 5% or more and 20% or less, and more preferably 8% or more. It is also preferred that aluminum silicate has a solid acid ($H^+$) in the structure. The above-described adsorbent (A) is specifically exemplified by "KYOWAAD® 700" manufactured by Kyowa Chemical Industry Co., Ltd. and "Nikkagel S" manufactured by Toshin Chemicals Co., Ltd.

The form of the adsorbent (A) is not particularly restricted and may be any one of powder, particle, sheet and fiber. A usage amount of the adsorbent (A) is not categorically restricted, since the usage amount is determined in accordance with a relationship between an amount of impurity to be adsorbed or a content of coenzyme Q10 in the solution and an adsorption capacity, and a treatment condition. A usage amount of the adsorbent (A) to a volume of the coenzyme Q10-containing solution may be generally 0.01 to 70% by weight, and preferably 0.1 to 10% by weight. Alternatively, a usage amount of the adsorbent (A) to a weight of coenzyme Q10 to be treated may be generally 1 to 200%, preferably 3 to 100%, and more preferably 5 to 75%. A usage amount of the adsorbent (A) to the weight of coenzyme Q10 to be treated in the case of the batch extraction may be, for example, 10 to 200%, preferably 20 to 100%, and more preferably 30 to 75%. In the case of the continuous extraction, even a smaller amount of the adsorbent (A) shows the similar effect, and a usage amount of the adsorbent (A) to the weight of coenzyme Q10 to be treated may be, for example, 1 to 100%, preferably 1 to 75%, and even more preferably 3 to 50%.

Even when only the above-described adsorbent (A) is used, the effect can be sufficiently obtained. In addition, when an adsorbent (B) which is different from the adsorbent (A) is used in addition to the adsorbent (A) in combination, coenzyme Q10 can be purified more efficiently. The adsorbent (B) except for an adsorbent of which main component is aluminum silicate is not particularly restricted, and a general adsorbent can be appropriately selected. Whether a filter medium has an adsorption performance or not, a filter medium can be used as the adsorbent (B). The adsorbent (B) is preferably exemplified by activated carbon, an adsorbent mainly composed of activated carbon, a synthetic adsorbent obtained by copolymerizing styrene and divinylbenzene, a phenol-formaldehyde resin adsorbent, an aldehyde adsorbent, magnesium silicate, aluminum hydroxide, aluminum oxide, magnesium oxide, a solid solution of aluminum oxide and magnesium oxide, diatomite, activated alumina, silica gel, silica-magnesia gel, an adsorbent obtained by chemically binding an alkyl group or an allyl group on an inorganic carrier, an aromatic adsorbent, a methacrylate ester adsorbent, synthetic zeolite, and a pearlite filter. A plurality of the adsorbents may be mixed to be used. Among the examples, silica gel, silica magnesia gel, aluminum hydroxide, magnesium silicate, aluminum oxide, magnesium oxide, a solid solution of aluminum oxide and magnesium oxide, a pearlite filter, and a combination thereof are preferred, and aluminum hydroxide, a solid solution of aluminum oxide and magnesium oxide, and a pearlite filter are more preferred.

A form of the adsorbent (B) is not particularly restricted and may be any one of powder, particle, sheet and fiber. A usage amount of the adsorbent (B) is not categorically restricted, since the usage amount is determined depending on an amount of impurity to be adsorbed, a content amount of coenzyme Q10 in the solution and an adsorption capacity of the adsorbent. The usage amount by weight to the volume of the coenzyme Q10-containing solution to be used may be generally 0.01 to 70%, and preferably 0.1 to 10%. Alternatively, the usage amount to the weight of the coenzyme Q10 to be treated may be generally 1 to 200%, preferably 2 to 100%, and more preferably 3 to 75%.

With respect to a ratio of the usage amounts of the adsorbent (A) and adsorbent (B), adsorbent (A): adsorbent (B) by weight may be, for example, 5:95 to 100:0, preferably 10:90 to 90:10, more preferably 30:70 to 70:30, and even more preferably 40:60 to 60:40. By adjusting the usage amount ratio of the adsorbent (A) and adsorbent (B) to the above-described range, an impurity removal rate can become high and high purity coenzyme Q10 can be obtained with high yield.

An adsorption treatment can be conducted in any one of a batch manner, a semi-batch manner, a continuous manner, a fluidized-bed manner and a fixed-bed manner. For example, an adsorption treatment can be conducted as the following method: the coenzyme Q10 solution is contacted with the adsorbent (A) by adding the adsorbent (A) or a mixture of the adsorbent (A) and adsorbent (B) to the coenzyme Q10 solution and stirring the obtained mixture; the coenzyme Q10 solution is contacted with the adsorbent (A) by immersing a sheet composed of the adsorbent (A) or a mixture of the adsorbent (A) and adsorbent (B) as a raw material into the coenzyme Q10 solution; the coenzyme Q10 solution is contacted with the adsorbent (A) by filling a tubular column with the adsorbent (A) or a mixture of the adsorbent (A) and adsorbent (B) and flowing the extract solution containing coenzyme Q10 through the column. In addition, when the adsorbent (A) and adsorbent (B) are used in combination, an adsorption treatment may be conducted by adding each of the adsorbent (A) or adsorbent (B) to the coenzyme Q10 solution and then adding the other adsorbent (B) or adsorbent (A); filling a tubular column with the adsorbent (A) and adsorbent (B) in two layers or filling separate columns with the adsorbent (A) and adsorbent (B) and flowing the extract solution containing coenzyme Q10 through the column or columns. Industrially, the method for contacting the coenzyme Q10 solution with the adsorbent (A) by filling a column with the adsorbent (A) or a mixture of the adsorbent (A) and adsorbent (B) as described above and flowing the extract solution containing coenzyme Q10 through the column is preferred, since the adsorbent can be easily separated and a usage amount of the adsorbent to the coenzyme Q10 to be treated can be small. In any one of the above-described methods, a time to contact the adsorbent and the coenzyme Q10 solution is not particularly restricted, and may be generally 5 minutes or more, preferably 10 minutes or more, and more preferably 15 minutes or more. The upper limit of the time is not particularly restricted, and for example, 12 hours is sufficient.

The temperature for the adsorption treatment is not particularly restricted, and may be generally in the range of −20° C. to 80° C., preferably −10 to 60° C., and more preferably 0 to 30° C.

The solvent of the coenzyme Q10 solution at the time of the adsorption treatment is not particularly restricted as long as the solvent is an organic solvent capable of dissolving coenzyme Q10. When the extract of the coenzyme Q10- producing microorganism itself or the concentrated extract is subjected to the adsorption treatment, the solvent is selected from the organic solvent for the extraction. Another organic solvent may be added to the extract of a coenzyme Q10-producing microorganism, or the solvent of the extract may be replaced with another organic solvent to obtain the coenzyme Q10 solution and the coenzyme Q10 solution may be subjected to the adsorption treatment. Alternatively, impurity is removed from the extract of the coenzyme Q10-producing microorganism to some extent by other method, and the thus obtained extract may be subjected to the adsorption treatment. The solvent of the coenzyme Q10 solution at the time of the adsorption treatment is specifically exemplified by a hydrocarbon solvent, a fatty acid ester solvent, an ether solvent, an alcohol solvent, a fatty acid solvent, a ketone solvent, a nitrogen compound solvent such as a nitrile solvent and an amide solvent, and a sulfur compound solvent.

As a hydrocarbon solvent is not particularly restricted and is exemplified by an aliphatic hydrocarbon solvent, an aromatic hydrocarbon solvent and a halogenated hydrocarbon solvent. Among the examples, an aliphatic hydrocarbon solvent and an aromatic hydrocarbon solvent are preferred, and an aliphatic hydrocarbon solvent is more preferred.

An aliphatic hydrocarbon solvent may be cyclic or non-cyclic and saturated or unsaturated, is not particularly restricted, and a saturated aliphatic hydrocarbon solvent is preferably used. In general, a $C_{3-20}$ aliphatic hydrocarbon solvent is used, a $C_{5-12}$ aliphatic hydrocarbon solvent is preferably used, and a $C_{5-8}$ aliphatic hydrocarbon solvent is more preferably used. An aliphatic hydrocarbon solvent is specifically exemplified by propane, butane, isobutane, pentane, 2-methylbutane, hexane, 2-methylpentane, 2,2-dimethylbutane, 2,3-dimethylbutane, heptane, a heptane isomer, such as 2-methylhexane, 3-methylhexane, 2,3-dimethylpentane and 2,4-dimethylpentane, octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane and cyclohexene, preferably pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane and p-menthane, more preferably pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane and ethylcyclohexane, even more preferably pentane, hexane, cyclohexane and methylcyclohexane, and particularly preferably hexane, heptane and methylcyclohexane.

An aromatic hydrocarbon solvent is not particularly restricted, and a $C_{6-20}$ aromatic hydrocarbon solvent is generally used, a $C_{6-12}$ aromatic hydrocarbon solvent is preferably used, and a $C_{7-10}$ aromatic hydrocarbon solvent is more preferably used. An aromatic hydrocarbon solvent is specifically exemplified by benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene and styrene, preferably toluene, xylene, o-xylene, m-xylene, p-xylene, ethylbenzene, cumene, mesitylene, tetralin, butylbenzene, p-cymene, cyclohexylbenzene, diethylbenzene and pentylbenzene, more preferably toluene, xylene, o-xylene, m-xylene, p-xylene, cumene and tetralin, and most preferably cumene.

A halogenated hydrocarbon solvent may be cyclic or non-cyclic and saturated or unsaturated, is not particularly restricted, and a non-cyclic halogenated hydrocarbon solvent is preferably used. A halogenated hydrocarbon solvent is more preferably a chlorinated hydrocarbon solvent and a fluorinated hydrocarbon solvent, and even more preferably a chlorinated hydrocarbon solvent. In addition, a $C_{1-6}$ halogenated hydrocarbon solvent may be used, a $C_{1-4}$ halogenated hydrocarbon solvent is preferably used, and a $C_{1-2}$ halogenated hydrocarbon solvent is more preferably used. Specifically, a halogenated hydrocarbon solvent is exemplified by dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene and 1,1,1,2-tetrafluoroethane, preferably dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane, and more preferably dichloromethane, chloroform, 1,2-dichloroethylene, trichloroethylene, chlorobenzene and 1,1,1,2-tetrafluoroethane.

A fatty acid ester solvent is not particularly restricted, and is exemplified by a propionate ester, an acetate ester and a formate ester, preferably an acetate ester and a formate ester, and more preferably an acetate ester. An ester group is not particularly restricted, and a $C_{1-8}$ alkyl ester and a $C_{7-12}$ aralkyl ester are generally used, a $C_{1-6}$ alkyl ester is preferably used, and a $C_{1-4}$ alkyl ester is more preferably used.

A propionate ester is specifically exemplified by methyl propionate, ethyl propionate, butyl propionate and isopentyl propionate, and preferably ethyl propionate.

An acetate ester is specifically exemplified by methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate and benzyl acetate, preferably methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate, more preferably methyl acetate, ethyl acetate, propyl acetate, isopropyl acetate, butyl acetate and isobutyl acetate, and most preferably ethyl acetate.

A formate ester is exemplified by methyl formate, ethyl formate, propyl formate, isopropyl formate, butyl formate, isobutyl formate, sec-butyl formate and pentyl formate, preferably methyl formate, ethyl formate, propyl formate, butyl formate, isobutyl formate and pentyl formate, and most preferably ethyl formate.

An ether solvent may be cyclic or non-cyclic and saturated or unsaturated, is not particularly restricted, and a saturated ether solvent is generally used. In general, a $C_{3-20}$ ether solvent is used, a $C_{4-12}$ ether solvent is preferably used, and a $C_{4-8}$ ether solvent is more preferably used. An ether solvent is specifically exemplified by diethyl ether, methyl tert-butyl ether, dipropyl ether, diisopropyl ether, dibutyl ether, dihexyl ether, ethyl vinyl ether, butyl vinyl ether, anisole, phenetol, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether and ethylene glycol monobutyl ether, preferably diethyl ether, methyl tert-butyl ether, dipropyl ether, diisopropyl ether, dibutyl ether, dihexyl ether, anisole, phenetol, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether, more preferably diethyl ether, methyl tert-butyl ether, anisole, dioxane, tetrahydrofuran, ethylene glycol monomethyl ether and ethylene glycol monoethyl ether, more preferably diethyl ether, methyl tert-butyl ether and anisole, and most preferably methyl tert-butyl ether.

An alcohol solvent may be cyclic or non-cyclic and saturated or unsaturated, is not particularly restricted, and a saturated alcohol solvent is generally used. In general, a $C_{1-20}$ alcohol solvent is used, a $C_{1-12}$ alcohol solvent is preferably used, and a $C_{1-6}$ alcohol solvent is more preferably used. In particular, a $C_{1-5}$ monovalent alcohol solvent, a $C_{2-5}$ divalent alcohol solvent and a $C_3$ trivalent alcohol solvent are preferred.

An alcohol solvent is specifically exemplified by a monovalent alcohol solvent such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol and 4-methylcyclohexanol; a divalent alcohol solvent such as 1,2-ethanediol, 1,2-propanediol, 1,3-propanediol, 1,2-butanediol, 1,3-butanediol, 1,4-butanediol, 2,3-butanediol and 1,5-pentanediol; and a trivalent alcohol solvent such as glycerin.

A monovalent alcohol solvent is preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol or 4-methylcyclohexanol, more preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol or cyclohexanol, more preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol or neopentyl alcohol, particularly preferably methanol, ethanol, 1-propanol, 2-propanol, 1-butanol, 2-butanol, isobutyl alcohol, 2-methyl-1-butanol or isopentyl alcohol, and most preferably 2-propanol.

A divalent alcohol solvent is preferably 1,2-ethanediol, 1,2-propanediol or 1,3-propanediol, and most preferably 1,2-ethanediol. A trivalent alcohol solvent is preferably glycerin.

A fatty acid solvent is exemplified by formic acid, acetic acid and propionic acid, preferably formic acid and acetic acid, and most preferably acetic acid.

A ketone solvent is not particularly restricted, and a $C_{3-6}$ ketone solvent is preferably used. A ketone solvent is specifically exemplified by acetone, methyl ethyl ketone, methyl butyl ketone and methyl isobutyl ketone, preferably acetone and methyl ethyl ketone, and most preferably acetone.

A nitrile solvent may be cyclic or non-cyclic and saturated or unsaturated, is not particularly restricted, and a saturated nitrile solvent is generally used. In general, a $C_{2-20}$ nitrile solvent is used, a $C_{2-12}$ nitrile solvent is preferably used, and a $C_{2-8}$ nitrile solvent is more preferably used.

A nitrile solvent is specifically exemplified by acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenyl cyclohexanecarbonitrile and tolylcyclohexanecarbonitrile.

A nitrile solvent is preferably acetonitrile, propionitrile, succinonitrile, butyronitrile, isobutyronitrile, valeronitrile, methyl cyanoacetate, ethyl cyanoacetate, benzonitrile, tolunitrile or chloropropionitrile, more preferably acetonitrile, propionitrile, butyronitrile or isobutyronitrile, and most preferably acetonitrile.

A nitrogen compound solvent except for a nitrile solvent is exemplified by an amide solvent such as formamide, N-methylformamide, N,N-dimethylformamide, N,N-dimethylacetamide and N-methylpyrrolidone; nitromethane; triethylamine and pyridine.

A sulfur compound solvent is exemplified by dimethyl sulfoxide and sulfolane.

It is preferred to select an organic solvent in consideration of the boiling point, melting point, viscosity or the like. For example, it is preferred that the boiling point is included in the range of about 30 to 150° C. at 1 atmosphere, since the solvent having such a boiling point can be easily removed for drying wet cells and recovered from a filtrate of crystallization. The melting point may be about 0° C. or higher, preferably about 10° C. or higher, and more preferably about 20° C. or higher, since the solvent having such a melting point is hardly solidified in the case of using the solvent at room temperature and cooling the solvent to room temperature or lower. The viscosity is preferably low as about 10 cp or lower at 20° C. in consideration of handling and a reduction of product loss.

Among the above-described organic solvent, for the purpose of efficiently removing impurity from the extract of the coenzyme Q10-producing microorganism, it is preferred to use a hydrophobic organic solvent or a solvent containing a hydrophobic organic solvent. In addition, it is preferred that the solvent to be used does not contain a large amount of water, since coenzyme Q10 is prevented from being adsorbed on the adsorbent. An amount of water contained in the solvent to be used by weight may be 15% or less at most, preferably 10% or less, and more preferably 6% or less.

The hydrophobic organic solvent used in the above-described case is not particularly restricted, and a hydrophobic solvent among the above-described organic solvent may be used. The hydrophobic organic solvent is preferably a hydrocarbon solvent, a fatty acid ester solvent or an ether solvent, more preferably a fatty acid ester solvent or a hydrocarbon solvent, and even more preferably an aliphatic hydrocarbon solvent. Among the aliphatic hydrocarbon solvent, a $C_{5-8}$ aliphatic hydrocarbon solvent is preferably used. The $C_{5-8}$ aliphatic hydrocarbon solvent is specifically exemplified by pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane and ethylcyclohexane, particularly preferably hexane, heptane and methylcyclohexane, and most preferably hexane. As the fatty acid ester solvent, ethyl acetate is preferably used.

The coenzyme Q10 solution is contacted with the adsorbent (A) as described above to selectively adsorb impurity on the adsorbent (A), and then the adsorbent (A) on which the impurity is adsorbed is separated from the coenzyme Q10 solution to obtain the coenzyme Q10 having higher purity. When the adsorbent (A) and adsorbent (B) are used in combination, the adsorbent (A) and adsorbent (B) respectively or a mixture of the adsorbent (A) and adsorbent (B) may be separated and removed from the coenzyme Q10 solution depending on the combination form. Hereinafter, the adsorbent (A), the adsorbent (B) or a mixture of the adsorbent (A) and the adsorbent (B) is simply referred to as "the adsorbent" in some cases. A method for separating the adsorbent after the adsorption treatment from the coenzyme Q10 is not particularly restricted and is exemplified by centrifugation, natural filtration, suction filtration, pressure filtration and centrifugal filtration. In addition, when a column which is filled with the adsorbent is used, it is not needed to perform a separation/removal procedure and the coenzyme Q10 solution eluted from the column can be directly used in the next step.

The used adsorbent may be discarded after each time of the treatment, or may be used again as long as an adsorption ability remains. For example, a column is filled with the adsorbent, the column can be continuously used as long as a target impurity can be effectively removed. In addition, a part of the adsorbent is discarded, and the adsorbent after use and the new adsorbent may be mixed to be used. Furthermore, the adsorbent may be subjected to regeneration treatment by washing with a solvent, such as hexane, ethyl acetate, isopropyl alcohol and a mixed solvent thereof, to be recycled.

As impurity to be removed by the above-described adsorption treatment, a sterol derivative is mainly exemplified as a component derived from the coenzyme Q10-producing microorganism.

Such a sterol derivative is not particularly restricted and exemplified by cholesterol, campesterol, desmosterol, brassicasterol, stigmasterol, α-sitosterol, β-sitosterol, dihydro-β-sitosterol, γ-sitosterol, 7-dehydrocholesterol, ergosterol and 22-dihydroergosterol. In addition, a sterol ester having an ester bond at the end of the sterol derivative is also included in the range of the impurity. A plurality of the above examples can be adsorbed to be removed. It is preferred to selectively adsorb a sterol fatty acid ester, and more specifically ergosterol, since a large amount of a sterol fatty acid ester is contained in a culture product after plant cells, yeast or the like is cultivated and it is difficult to separate and remove a sterol fatty acid ester by other method such as crystallization.

The yield of coenzyme Q10 in the solution after the adsorption treatment in comparison with the solution before the adsorption treatment may be generally 85% or more, and preferably 90% or more. The yield may be 99% or less.

A purity improvement percent point may be generally 2 percent point or more, preferably 2.5 percent point or more, and for example, 10 percent point or less, particularly 7 percent point or less. The purity improvement percent point corresponds to the difference of weight percent of Q10 in two non-volatile constituents obtained by drying the solutions before and after the adsorption treatment.

A removal rate of ergosterol removed by the above-described adsorption treatment may be generally 2% or more, preferably 30% or more, more preferably 40% or more, and preferably 100% or less, generally 90% or less, or 60% or less.

By the above-described procedures, coenzyme Q10 is extracted in an organic solvent from the microorganism cells containing coenzyme Q10, microorganism cell homogenate, aqueous dispersion of the microorganism cell homogenate, dried microorganism cells, or dried microorganism cell homogenate, and the extract is subjected to the adsorption treatment in order to purify and recover coenzyme Q10 having improved purity. The coenzyme Q10 solution after the adsorption treatment can be directly used, and the coenzyme Q10 solution separated from the adsorbent may be further treated to obtain a coenzyme Q10-containing composition or a coenzyme Q10 crystal having a more preferred form or higher purity. Such a treatment step is exemplified by concentration condensation, solvent exchange, oxidation, reduction, column chromatography, crystallization, and a combination thereof. For example, a solvent may be distilled away from the coenzyme Q10 solution separated from the adsorbent for concentration condensation to obtain purified coenzyme Q10. Alternatively, after coenzyme Q10 is further purified by column chromatography using silica gel or the like as needed, a solvent may be distilled away to obtain purified coenzyme Q10. Furthermore, the target coenzyme Q10 may be obtained as a crystal by crystallization procedure. Before the above-described column chromatography, oxidation, reduction and crystallization, a solvent may be exchanged as needed. For example, coenzyme Q10 is extracted in an organic solvent from the coenzyme Q10-producing microorganism, the obtained extract containing coenzyme Q10 is subjected to the adsorption treatment, oxidation or reduction is conducted before or after the adsorption treatment as needed, and highly pure coenzyme Q10 can be obtained as a crystal by a crystallization procedure.

In order to produce only reduced coenzyme Q10 or coenzyme Q10 of which reduced coenzyme Q10 ratio is high as coenzyme Q10, only reduced coenzyme Q10 or coenzyme Q10 of which reduced coenzyme Q10 ratio is high can be obtained without special treatment by using a microorganism which can produce coenzyme Q10 having high reduced coenzyme Q10 ratio as the coenzyme Q10-producing microorganism and conducting the above-described extraction and adsorption treatment under an antioxidant atmosphere, for example, under an inert atmosphere such as nitrogen gas. It is possible that a reduced coenzyme Q10 ratio can be further increased by reducing the thus obtained coenzyme Q10 having high reduced coenzyme Q10 ratio. In addition, the coenzyme Q10-containing extract having relatively low reduced coenzyme Q10 ratio such as not more than 50 mol % or not more than 30 mol % without antioxidant means or due to oxidation by oxygen in the air and oxidant is subjected to the adsorption treatment of the present invention production method and then a reduction reaction in order to produce coenzyme Q10 having high reduced coenzyme Q10 ratio. For the purpose of producing reduced coenzyme Q10, it is preferred that a reduced coenzyme Q10 ratio in the final production step or of the final product is high and a reduced coenzyme Q10 ratio in a total amount 100 mol % of coenzyme Q10 may be, for example, 70 mol % or more, preferably 80 mol % or more, more preferably 90 mol % or more, and even more preferably 96 mol % or more.

As the more specific one embodiment, coenzyme Q10 is extracted in an organic solvent from the coenzyme Q10-producing microorganism, the thus obtained extract containing coenzyme Q10 is subjected to the adsorption treatment, coenzyme Q10 is further purified by column chromatography, a reduction treatment is conducted, and a crystal of highly pure reduced coenzyme Q10 is obtained by crystallization.

The production method can be also used for producing oxidized coenzyme Q10. In such a case, the coenzyme Q10 having high oxidized coenzyme Q10 ratio can be obtained by simple procedure. For example, coenzyme Q10 is extracted in an organic solvent from the microorganism cells, microorganism cell homogenate, aqueous dispersion of the microorganism cell homogenate, dried microorganism cells, or dried microorganism cell homogenate containing coenzyme Q10, and thus obtained extract may be subjected to an oxidation treatment by an oxidant before or after the adsorption treatment. Alternatively, the coenzyme Q10 having high oxidized coenzyme Q10 ratio can be obtained due to natural oxidation by merely conducting extraction, adsorption, other purification and aftertreatment in the air or drying the microorganism cells in the air before the extraction.

As the more specific one embodiment, coenzyme Q10 is extracted in an organic solvent from the coenzyme Q10-producing microorganism, the thus obtained extract containing coenzyme Q10 is subjected to the adsorption treatment, the solvent of the extract is exchanged, coenzyme Q10 is further purified by column chromatography, an oxidation treatment is conducted, and a crystal of highly pure oxidized coenzyme Q10 is obtained by crystallization.

EXAMPLES

Hereinafter, the present invention is described in more detail with Examples and Comparative examples but is not restricted to the following Examples. In addition, the yield and purity of coenzyme Q10 in Examples and Comparative examples do not represent the limiting value of the present invention nor the upper limit.

The yield of coenzyme Q10 was calculated by analyzing the coenzyme Q10 concentrations in the solutions before and after the adsorption treatment. The concentration of coenzyme Q10 was measured by high-performance liquid chromatography (HPLC) (manufactured by SHIMADZU) in the following condition.

HPLC Measurement Condition
Column: YMC-Pack ODS-A manufactured by YMC
Oven temperature: 30° C.
Mobile phase: methanol/hexane=85/15 by volume
Flow rate: 1.0 ml/min
Detection: UV 275 nm A purity improvement percent point of coenzyme Q10 was calculated as the difference of weight percent of Q10 in two non-volatile constituents obtained by drying the solutions before and after the adsorption treatment.

A removal rate of ergosterol was calculated by measuring ergosterol concentrations in the solutions before and after the adsorption treatment and using the following formula. The ergosterol concentration is described as ERG concentration and was measured by using HPLC in the same condition as the above-described measurement condition of coenzyme Q10 concentration.

Removal rate of ergosterol={(ERG concentration before the adsorption treatment−ERG concentration after the adsorption treatment)/(ERG concentration before the adsorption treatment)}×100

Example 1

*Saitoella complicata* IFO10748 strain, which could produce coenzyme Q10, was aerobically cultivated in a culture medium (peptone 5 g/L, yeast extract 3 g/L, extract malt 3 g/L, glucose 20 g/L, pH 6.0) at 25° C. for 160 hours. The obtained microorganism culture medium containing coenzyme Q10 was concentrated by centrifugation, and the microorganism cells were dried by using a spray dryer. To the obtained dried microorganism, 1.5 times amount of hexane to the volume of the culture medium before the centrifugation was added. The mixture was stirred at 50° C. for 1 hour to extract coenzyme Q10. The extract of the coenzyme Q10-producing microorganism was concentrated so that the coenzyme Q10 concentration was adjusted to 25 g/L. The reduced coenzyme Q10 ratio in the concentrate, i.e. the ratio of reduced coenzyme Q10 in the total coenzyme Q10, was about 5 wt %. Into the concentrated extract, 50 wt % to the wt % of coenzyme Q10 of KYOWAAD® 700 (manufactured by Kyowa Chemical Industry Co., Ltd., KW700SN) composed of synthetic aluminum silicate as the adsorbent (A) and KYOWAAD® 200 (manufactured by Kyowa Chemical Industry Co., Ltd., KW200) composed of aluminum hydroxide as the adsorbent (B) were respectively added. The mixture was stirred at room temperature for 1 hour and then filtrated. The filtrate was analyzed; as a result, it was confirmed that the yield of coenzyme Q10 was 98.41%, the purity thereof was increased by 3.4 percent point, and the removal rate of ergosterol was 49.7%.

Example 2

Into the concentrated extract of the coenzyme Q10-producing microorganism obtained similarly to Example 1, 50 wt % to the wt % of coenzyme Q10 of KYOWAAD® 700 (manufactured by Kyowa Chemical Industry Co., Ltd., KW700SN) as the adsorbent (A) and pearlite filter medium Rokahelp (manufactured by MITSUI MINING & SMELTING CO., LTD.) as the adsorbent (B) were respectively added. The mixture was subjected to the adsorption treatment in a similar condition to Example 1. As a result, the yield of coenzyme Q10 was 98.97%, the purity thereof was increased by 2.8 percent point, and the removal rate of ergosterol was 54.7%.

Example 3

Into the concentrated extract of the coenzyme Q10-producing microorganism obtained similarly to Example 1, 50 wt % to the wt % of coenzyme Q10 of KYOWAAD® 700

(manufactured by Kyowa Chemical Industry Co., Ltd., KW700SN) as the adsorbent (A) and a solid solution of aluminum oxide and magnesium oxide KYOWAAD® 2000 (manufactured by Kyowa Chemical Industry Co., Ltd., KW2000) as the adsorbent (B) were respectively added. The mixture was subjected to the adsorption treatment in a similar condition to Example 1. As a result, the yield of coenzyme Q10 was 96.26%, the purity thereof was increased by 4.4 percent point, and the removal rate of ergosterol was 37.6%.

Example 4

The microorganism culture medium which was obtained by the cultivation similarly to Example 1 and which contained coenzyme Q10 was concentrated by centrifugation, and the supernatant was separated to be removed. The obtained heavy layer was subjected to cell disruption under pressure of about 100 MPa to obtain concentrated microorganism culture medium. Into the culture medium, hexane and isopropanol were added as extraction solvents to extract coenzyme Q10. The extract of the coenzyme Q10-producing microorganism was concentrated so that the coenzyme Q10 concentration was adjusted to 25 g/L. Into the extract, 9 wt % to the wt % of coenzyme Q10 of KYOWAAD® 700 (manufactured by Kyowa Chemical Industry Co., Ltd., KW700SN) as the adsorbent (A) was added. The mixture was stirred at room temperature for 1 hour and then filtrated. The filtrate was analyzed; as a result, the yield of coenzyme Q10 was 93.83%, the purity thereof was increased by 3.3 percent point, and the removal rate of ergosterol was 2.8%.

Example 5

Into the concentrated extract of the coenzyme Q10-producing microorganism obtained similarly to Example 1, 50 wt % to the wt % of coenzyme Q10 of KYOWAAD® 700 (manufactured by Kyowa Chemical Industry Co., Ltd., KW700SN) as the adsorbent (A) and similarly synthetic aluminum silicate Nikkagel S (manufactured by Toshin Chemicals Co., Ltd.) were respectively added. The mixture was subjected to the adsorption treatment in a similar condition to Example 1. As a result, the yield of coenzyme Q10 was 95.17%, the purity thereof was increased by 2.9 percent point, and the removal rate of ergosterol was 39.4%.

Example 6

*Saitoella complicata* IFO10748 strain, which could produce coenzyme Q10, was aerobically cultivated in a culture medium (peptone 5 g/L, yeast extract 3 g/L, extract malt 3 g/L, glucose 20 g/L, pH 6.0) at 25° C. for 160 hours. The obtained microorganism culture medium containing coenzyme Q10 was concentrated by centrifugation, and the microorganism cells were dried by using a spray dryer. To the obtained dried microorganism, 1.5 times amount of ethyl acetate to the volume of the culture medium before the centrifugation was added. The mixture was stirred at 50° C. for 1 hour to extract coenzyme Q10. The extract of the coenzyme Q10-producing microorganism was concentrated so that the coenzyme Q10 concentration was adjusted to 25 g/L. The reduced coenzyme Q10 ratio in the concentrate was about 5 wt %. Into the concentrated extract, 50 wt % to the wt % of coenzyme Q10 of KYOWAAD® 700 (manufactured by Kyowa Chemical Industry Co., Ltd., KW700SN) as the adsorbent (A) and Rokahelp (manufactured by MITSUI MINING & SMELTING CO., LTD.) as the adsorbent (B) were respectively added. The mixture was stirred at room temperature for 1 hour and then filtrated. The filtrate was analyzed; as a result, it was confirmed that the yield of coenzyme Q10 was 94.11%, the purity thereof was increased by 5.4 percent point, and the removal rate of ergosterol was 38.2%.

Comparative Example 1

Into the concentrated extract of the coenzyme Q10-producing microorganism obtained similarly to Example 1, 50 wt % to the wt % of coenzyme Q10 of KYOWAAD® 200 (manufactured by Kyowa Chemical Industry Co., Ltd., KW200) and Rokahelp (manufactured by MITSUI MINING & SMELTING CO., LTD.) were respectively added. The mixture was subjected to the adsorption treatment in a similar condition to Example 1. As a result, it was confirmed that the yield of coenzyme Q10 was 96.46%, the purity thereof was merely increased by 1.5 percent point, and the removal rate of ergosterol was 10.7%.

Comparative Example 2

Into the concentrated extract of the coenzyme Q10-producing microorganism obtained similarly to Example 1, 50 wt % to the wt % of coenzyme Q10 of Rokahelp (manufactured by MITSUI MINING & SMELTING CO., LTD.) was added. The mixture was subjected to the adsorption treatment in a similar condition to Example 1. As a result, the yield of coenzyme Q10 was 94.05%, the purity thereof was increased by 0 percent point, and the removal rate of ergosterol was 2.0%.

Comparative Example 3

Into the concentrated extract of the coenzyme Q10-producing microorganism obtained similarly to Example 1, 50 wt % to the wt % of coenzyme Q10 of KYOWAAD® 2000 (manufactured by Kyowa Chemical Industry Co., Ltd., KW2000) and Rokahelp (manufactured by MITSUI MINING & SMELTING CO., LTD.) were respectively added. The mixture was subjected to the adsorption treatment in a similar condition to Example 1. As a result, it was confirmed that the yield of coenzyme Q10 was 82.82%, the purity thereof was merely increased by 1.8 percent point, and the removal rate of ergosterol was 4.1%.

Comparative Example 4

Into the concentrated extract of the coenzyme Q10-producing microorganism obtained similarly to Example 1, 50 wt % to the wt % of coenzyme Q10 of magnesium silicate KYOWAAD® 600 (manufactured by Kyowa Chemical Industry Co., Ltd., KW600) and Rokahelp (manufactured by MITSUI MINING & SMELTING CO., LTD.) were respectively added. The mixture was subjected to the adsorption treatment in a similar condition to Example 1. As a result, it was confirmed that the yield of coenzyme Q10 was 96.29%, the purity thereof was merely increased by 1.3 percent point, and the removal rate of ergosterol was 4.2%.

Comparative Example 5

Into the concentrated extract of the coenzyme Q10-producing microorganism obtained similarly to Example 1, 50 wt % to the wt % of coenzyme Q10 of activated carbon and Rokahelp (manufactured by MITSUI MINING &

SMELTING CO., LTD.) were respectively added. The mixture was subjected to the adsorption treatment in a similar condition to Example 1. As a result, it was confirmed that the yield of coenzyme Q10 was 89.99%, the purity thereof was merely increased by 0.3 percent point, and the removal rate of ergosterol was 29.7%.

Comparative Example 6

Into the concentrated extract of the coenzyme Q10-producing microorganism obtained similarly to Example 1, 50 wt % to the wt % of coenzyme Q10 of activated alumina 300 (manufactured by NACALAI TESQUE, INC.) and Rokahelp (manufactured by MITSUI MINING & SMELTING CO., LTD.) were respectively added. The mixture was subjected to the adsorption treatment in a similar condition to Example 1. As a result, it was confirmed that the yield of coenzyme Q10 was 96.78%, the purity thereof was merely increased by 1.6 percent point, and the removal rate of ergosterol was 1.1%.

adsorbent by using an elution solvent is required after the adsorption treatment to obtain coenzyme Q10.

An aspect of the present invention to solve the above-described problems is to provide a method for stably producing coenzyme Q10 with a simple coenzyme Q10 production step by efficiently removing impurity of a microorganism from an extract of coenzyme Q10-producing microorganism.

The inventors of the present invention intensively studied for solving the above problem. As a result, the present inventors completed the present invention by finding that the specific adsorbent is useful for efficiently purifying coenzyme Q10, since the adsorbent hardly adsorbs coenzyme Q10 itself but selectively adsorbs a component derived from cells of a coenzyme Q10-producing microorganism except for coenzyme Q10.

The present invention relates to a method for producing coenzyme Q10 characterized in comprising the step of contacting an extract of a coenzyme Q10-producing microorganism with an adsorbent (A), wherein a main component of the adsorbent (A) is aluminum silicate.

The present invention preferably relates to the above-described method wherein 50% or more of the adsorbent (A) is aluminum silicate.

The present invention preferably relates to the above-described method wherein an adsorbent (B) is used in addition to an adsorbent (A).

The present invention preferably relates to the above-described method wherein the adsorbent (B) is one or more selected from the group consisting of activated carbon, an adsorbent containing activated carbon as a main component, a synthetic adsorbent obtained by copolymerizing styrene and divinylbenzene, a phenol-formaldehyde resin adsorbent, an aldehyde adsorbent, magnesium silicate, aluminum hydroxide, aluminum oxide, magnesium oxide, silica gel,

TABLE 1

| | Raw material for extraction | Solvent | Adsorbent (A) | Adsorbent (B) | | Yield (%) | Purity improvement percent point (%) | Ergosterol removal rate (%) |
|---|---|---|---|---|---|---|---|---|
| Example 1 | non-disrupted dried cell | hexane | KW700SN (50 wt. %) | KW200 (50 wt %) | — | 98.41 | 3.4 | 49.7 |
| Example 2 | non-disrupted dried cell | hexane | KW700SN (50 wt %) | — | Rokahelp (50 wt %) | 98.97 | 2.8 | 54.7 |
| Example 3 | non-disrupted dried cell | hexane | KW700SN (50 wt %) | KW2000 (50 wt %) | — | 96.26 | 4.4 | 37.6 |
| Example 4 | heavy layer after disruption (iPrOH) | hexane | KW700SN (9 wt %) | — | — | 93.83 | 3.3 | 2.8 |
| Example 5 | non-disrupted dried cell | hexane | KW700SN (50 wt %) Nikkagel S (50 wt %) | — | — | 95.17 | 2.9 | 39.4 |
| Example 6 | non-disrupted dried cell | ethyl acetate | KW700SN (50 wt %) | — | Rokahelp (50 wt %) | 94.11 | 5.4 | 38.2 |
| Comparative example 1 | non-disrupted dried cell | hexane | — | KW200 (50 wt %) | Rokahelp (50 wt %) | 96.46 | 1.5 | 10.7 |
| Comparative example 2 | non-disrupted dried cell | hexane | — | — | Rokahelp (50 wt %) | 94.05 | 0.0 | 2.0 |
| Comparative example 3 | non-disrupted dried cell | hexane | — | KW2000 (50 wt %) | Rokahelp (50 wt %) | 82.82 | 1.8 | 4.1 |
| Comparative example 4 | non-disrupted dried cell | hexane | — | KW600 (50 wt %) | Rokahelp (50 wt %) | 96.29 | 1.3 | 4.2 |
| Comparative example 5 | non-disrupted dried cell | hexane | — | activated carbon (50 wt %) | Rokahelp (50 wt %) | 89.99 | 0.3 | 29.7 |
| Comparative example 6 | non-disrupted dried cell | hexane | — | activated alumina (50 wt %) | Rokahelp (50 wt %) | 96.78 | 1.6 | 1.1 |

The present application addresses improvement for easy and stably mass production of coenzyme Q10 at a low cost in the above-described conventional methods.

For example, with respect to the method of Patent document 1, when a large amount of impurity coexists, such as the case of an extract of coenzyme Q10-producing microorganism, it is difficult to obtain coenzyme Q10 having a high purity by crystallization only. Even when highly-pure coenzyme Q10 can be obtained, it is necessary to strictly control the operating condition such as crystallization operating temperature and the time required for the crystallization process is prolonged. With respect to the adsorption method of Patent document 2, since the purpose of the method is to adsorb coenzyme Q10 itself on an adsorbent, the step of separating and eluting coenzyme Q10 from the silica-magnesia gel, an adsorbent obtained by chemically binding an alkyl group or an allyl group on an inorganic carrier, diatomite, activated alumina, an aromatic adsorbent, a methacrylate ester adsorbent, synthetic zeolite, and a pearlite filter.

The present invention preferably relates to the above-described method, comprising the steps of separating the extract of the coenzyme Q10-producing microorganism contacted with the adsorbent (A) from the adsorbent (A) and further treating the separated extract.

The present invention preferably relates to the above-described method wherein the step of treating is one or more steps selected from a condensation, a solvent exchange, an oxidation, a reduction, a column chromatography and a crystallization.

According to the embodiments of the present invention, high quality coenzyme Q10 can be obtained successfully in terms of workability and economy with easily adsorbing impurity to be removed and without adsorbing coenzyme Q10 only by contacting a solution containing coenzyme Q10 with an adsorbent (A) having aluminum silicate as a main component.

In addition, an impurity removal efficiency can be further improved by using an adsorbent (B) different from the adsorbent (A) in addition to the adsorbent (A).

Obviously, numerous modifications and variations of the present invention are possible in light of the above teachings. It is therefore to be understood that within the scope of the appended claims, the invention may be practiced otherwise than as specifically described herein.

What is claimed is:

1. A method of producing coenzyme Q10, the method comprising:
    contacting an extract comprising coenzyme Q10 from a coenzyme Q10-producing microorganism with an adsorbent (A), wherein the adsorbent (A) adsorbs components of the extract other than coenzyme Q10, and a solution of the coenzyme Q10 having a higher purity compared to the extract is obtained,
    wherein the adsorbent (A) comprises 50% or more of aluminum silicate.

2. The method of claim 1, further comprising:
    before or after contacting the extract with the adsorbent (A), contacting the extract with an adsorbent (B).

3. The method of claim 2, wherein the adsorbent (B) is at least one selected from the group consisting of an adsorbent comprising activated carbon, a synthetic adsorbent obtained by copolymerizing styrene and divinylbenzene, a phenol-formaldehyde resin adsorbent, an aldehyde adsorbent, magnesium silicate, aluminum hydroxide, aluminum oxide, magnesium oxide, diatomite, activated alumina, silica gel, silica-magnesia gel, an adsorbent obtained by chemically binding an alkyl group or an allyl group on an inorganic carrier, an aromatic adsorbent, a methacrylate ester adsorbent, synthetic zeolite, and a pearlite filter medium.

4. The method of claim 2, wherein the adsorbent (B) comprises a pearlite filter medium.

5. The method of claim 1, wherein the contacting comprises contacting the extract with a mixture comprising the adsorbent (A) and an adsorbent (B).

6. The method of claim 5, wherein the adsorbent (B) is at least one selected from the group consisting of, an adsorbent comprising activated carbon, a synthetic adsorbent obtained by copolymerizing styrene and divinylbenzene, a phenol-formaldehyde resin adsorbent, an aldehyde adsorbent, magnesium silicate, aluminum hydroxide, aluminum oxide, magnesium oxide, diatomite, activated alumina, silica gel, silica-magnesia gel, an adsorbent obtained by chemically binding an alkyl group or an allyl group on an inorganic carrier, an aromatic adsorbent, a methacrylate ester adsorbent, synthetic zeolite, and a pearlite filter medium.

7. The method of claim 5, further comprising:
    separating the extract of the coenzyme Q10-producing microorganism contacted with the adsorbent (A) and the adsorbent (B) from the adsorbent (A) and the adsorbent (B); and
    treating the solution comprising the coenzyme Q10 separated from the absorbent (A) and the adsorbent (B).

8. The method of claim 7, wherein the treating comprises conducting a condensation, a solvent exchange, an oxidation, a reduction, a column chromatography, a crystallization, or a combination thereof.

9. The method of claim 5, wherein a weight ratio of the adsorbent (A) to the adsorbent (B) in the mixture is from 40: 60 to 60: 40.

10. The method of claim 5, wherein a weight ratio of the adsorbent (A) to the adsorbent (B) in the mixture is 50: 50.

11. The method of claim 1, further comprising:
    separating the extract contacted with the adsorbent (A) from the adsorbent (A); and
    treating the solution comprising the coenzyme Q10 from the absorbent (A).

12. The method of claim 11, wherein the treating comprises conducting a condensation, a solvent exchange, an oxidation, a reduction, a column chromatography, and a crystallization, or a combination thereof.

13. The method of claim 1, wherein the adsorbent (A) comprises 60% or more of aluminum silicate.

14. The method of claim 1, wherein the adsorbent (A) comprises 65% or more of aluminum silicate.

15. The method of claim 1, wherein the aluminum silicate comprises from 50% to 70% of silicon dioxide.

16. The method of claim 1, wherein the aluminum comprises from 55% to 65% of silicon dioxide.

17. The method of claim 1, wherein the aluminum silicate comprises crystal water.

18. The method of claim 1, wherein the aluminum silicate comprises a solid acid.

19. The method of claim 1, wherein upon the contacting, the adsorbent (A) absorbs ergosterol and thereby removes ergosterol from the extract, wherein a removal rate of ergosterol is 30% or more.

20. The method of claim 1, wherein upon the contacting, the adsorbent (A) absorbs ergosterol and thereby removes ergosterol from the extract, wherein a removal rate of ergosterol is 40% or more.

* * * * *